United States Patent [19]

Wallshein

[11] 4,302,532
[45] Nov. 24, 1981

[54] ORTHODONTIC BRACKET WITH PROTECTIVE INSERT OR LINER

[76] Inventor: Melvin Wallshein, 8645 Bay Pkwy., Brooklyn, N.Y. 11214

[21] Appl. No.: 698,915

[22] Filed: Jun. 23, 1976

[51] Int. Cl.³ .............................................. A61C 7/00
[52] U.S. Cl. ..................................................... 433/8
[58] Field of Search .................. 32/14 A, 14 B; 433/8

[56] References Cited

U.S. PATENT DOCUMENTS

| | | | |
|---|---|---|---|
| 2,908,974 | 10/1959 | Stifter | 32/14 A |
| 3,775,850 | 12/1973 | Northcott | 32/14 A |
| 3,964,165 | 6/1976 | Stahl | 32/14 A |

OTHER PUBLICATIONS

American Journal Orthodontic and Oral Surgery, Jul. 1938, p. 639.

*Primary Examiner*—Robert Peshock
*Attorney, Agent, or Firm*—Frishauf, Holtz, Goodman and Woodward

[57] ABSTRACT

A plastic orthodontic bracket has an insert in the arch wire opening thereof which is of a material harder than the plastic material from which the bracket is fabricated. Preferably, the insert or liner is a metal material. The bracket with the insert or liner may be made by molding the plastic material around the liner material or by molding the plastic bracket and later inserting a previously formed liner or insert. Alternatively, the bracket may be made by means of extrusion of a plastic material and/or the liner material, the resultant elongated structure being then cut up into sections to form the individual brackets.

34 Claims, 16 Drawing Figures

ORTHODONTIC BRACKET WITH PROTECTIVE INSERT OR LINER

This invention relates to orthodontic brackets, and more particularly to plastic orthodontic brackets having a liner or insert in the arch wire receiving opening thereof.

Plastic and metal orthodontic brackets are presently widely used. The metal brackets, while of high structural integrity, are unattractive in the mouth and are undesirable from an esthetic point of view. Plastic brackets, while being less obtrusive from an esthetic point of view, suffer from the disadvantage of being prone to damage, especially at the areas thereof which contact an arch wire. Arch wires in the arch wire openings of brackets generally apply high mechanical forces relative to the brackets. It has been found that arch wires cause portions around the arch wire openings of plastic brackets to break away, thus necessitating replacement of the plastic bracket in the mouth of the patient.

U.S. Pat. No. 3,930,311 illustrates an attempt to provide a reinforced plastic orthodontic bracket. However, the edges of the arch wire openings of brackets fabricated in accordance with U.S. Pat. No. 3,930,311 are still prone to damage due to the high forces applied by the arch wire relative to the bracket.

The object of the present invention is to provide an improved plastic orthodontic bracket which has improved resistance to damage due to the presence of the arch wire and which still possesses the attractive appearance value of plastic orthodontic brackets, especially such brackets which are made of translucent plastic material.

SUMMARY OF THE INVENTION

According to the present invention, an orthodontic bracket assembly comprises a non-metallic bracket having an arch wire receiving opening therein, and a hard liner on a surface portion of said bracket which defines said arch wire receiving opening, the hard liner being fabricated of a material harder than the material of the bracket. Preferably, the liner is fabricated from metal and/or the bracket is fabricated from a plastic material. The liner of the present invention is preferably fabricated to cover at least a substantial portion of the surface defining all of the edges of the bracket to protect the bracket from breakage due to, for example, forces applied by an arch wire. The central portions of the liner may comprise void spaces, if desired. Moreover, the liner may be dimensioned so that it extends a small distance short of the edges of the arch wire receiving opening while still effectively protecting the bracket from damage.

The composite bracket and liner structure of the present invention may be made by several methods discussed herein and defined in the appended claims.

DETAILED DESCRIPTION OF ILLUSTRATED EMBODIMENTS

Figure 1:
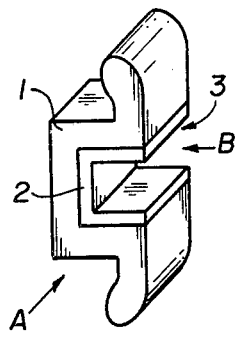
FIG. 1 illustrates a bracket utilizing an insert according to the present invention.

FIG. 1 shows a typical bracket 1 with a liner or insert 2 inserted in the arch wire opening thereof. The bracket portion 1 is fabricated of a plastic material and the insert 2 is fabricated of a harder material, such as metal. Typical plastic brackets 1, presently known in the art, are defective in that when an arch wire is placed in the arch wire opening 3 thereof, the forces exerted by the arch wire cause chipping or breakage of the plastic bracket 1. In accordance with the present invention, an insert 2 of harder material, such as metal, is inserted in the art wire opening 3 so that an arch wire inserted therein bears against the harder lining 2 and therefore does not cause damage to the plastic bracket. The hard lining 2 is relatively small in relation to the bracket 1 and detracts only slightly from the cosmetic appearance of the bracket 1. Since metallic arch wires are inserted in the arch wire openings 3, the provision of a metallic liner 2 only slightly increases the overall amount of metal used in the appliance and therefore, does not substantially detract from the appearance. The brackets 1 are preferably made of plastic such as polycarbonate.

The liner 2 may be molded directly in the plastic bracket 1, during fabrication of the plastic bracket 1. However, it has been found to also be advantageous to pre-mold the bracket portion 1 of plastic material and to later insert the liner 2, for example by sliding the liner 2 into the opening 3 of the bracket 1 in the direction of the arrow A shown in FIG. 1 or by inserting the liner 2 in the direction of the arrow B in FIG. 1. In either case, it has been found to be still further advantageous to apply ultrasonic energy to one or both of the bracket 1 and liner 2 during insertion so as to effectively weld the parts together in the final inserted state.

Figure 2:
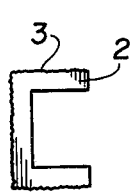
FIG. 2 is an enlarged view of an insert shown in FIG. 1.
Figure 6:
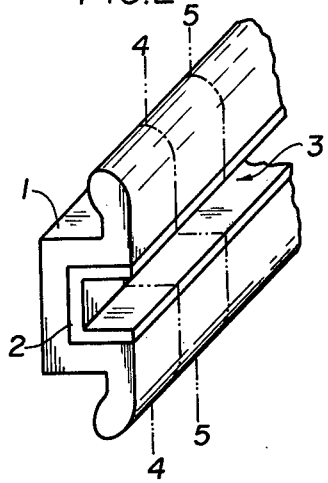
FIG. 6 is an illustration of a method of making the bracket of FIG. 1 by cutting an elongated assembly into sections.

FIG. 2 shows an enlarged view of a typical liner 2 having irregular or roughened outer surfaces 3, which may be, for example, serrated. By roughening the outer surface 3 as shown in FIG. 2, and by using ultrasonic energy as mentioned above when inserting the liner 2 in the bracket 1, still improved adhesion of the liner 2 to the plastic bracket 1 is obtained. During application of ultrasonic energy, localized heat is developed at the contact points between the plastic bracket 1 and the liner 2 to cause local melting of the plastic to better adhere or "weld" the liner 2 to the bracket 1. The bracket 2 may be fabricated as an elongated member, for example by extrusion, and then cut up to the desired short lengths prior to insertion in the plastic bracket 1. Alternatively, the plastic bracket and liner 2 may be both fabricated in elongated lengths, as shown in FIG. 6, the liner inserted in the opening 3 of the plastic bracket 1, and the resultant composite structure severed along the length thereof, for example along lines 4,5 etc., as shown in FIG. 6, to produce brackets of the desired size with the liners 2 already therein.

Figure 3:
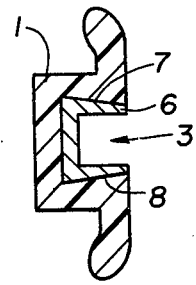
FIG. 3 is a sectional view of a modified form of the present invention.

FIG. 3 illustrates a modified form of a liner 6 inserted in a bracket 1. The outline of the liner 6 is generally trapezoidal and the sloping sides 7,8 thereof provide still better engagement of the liner 6 with the plastic bracket 1. The liner 6 is preferably inserted in the bracket 1 in a direction substantially parallel to the arch wire slot 3—that is, generally in the direction of the arrow A in FIG. 1. Ultrasonic energy may be applied to one or both of the bracket 1 and insert 6 during insertion, as desired.

Figure 4:
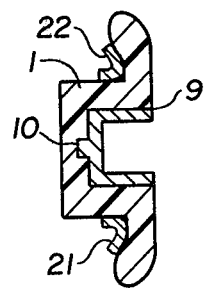
FIG. 4 is a sectional view of a still further modification of the present invention.

FIG. 4 shows a still further modified embodiment wherein the liner 9 has a protrusion 10 which is anchored in the plastic bracket 1. The liner 9 may be inserted in either of the directions A or B (FIG. 1). The liner 9 of FIG. 4, and the liner 6 of FIG. 3, are preferably formed by extrusion as elongated elements, and are cut up to the appropriate size before insertion into their respective brackets 1.

Figure 5:
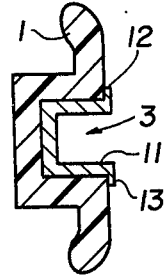
FIG. 5 is a cross-sectional view of yet a further modification of the present invention.

FIG. 5 shows a still further embodiment of the present invention wherein a liner 11 has overlapping lips or flanges 12,13. The lips 12,13 still further protect the plastic bracket 1 from damage due to the high forces applied to the bracket by an arch wire. This arrangement is particularly suitable for use in arrangements wherein a rectangular arch wire is engaged in the arch wire opening 3 and is then twisted axially to provide rotational forces to a tooth to which the bracket is mounted. In such a case, the lips 12,13 provide a greater structural integrity to the bracket and liner combination and enhance the protection to the plastic bracket. The liner 11 of FIG. 5 may be inserted in either direction A or B, as shown in FIG. 1, with or without the application of ultrasonic energy to one or both of the bracket 1 and liner 11.

Figure 7:
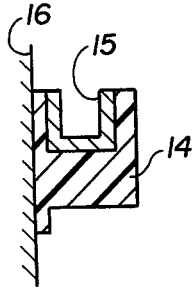
FIGS. 7, 8 and 9 show a different type of bracket with respective different liner arrangements therein.

FIG. 7 shows another type of bracket 14 generally in use in the orthodontic field with a liner 15 inserted therein. The liner 15 is similar to the liner of FIG. 2 and preferably has roughened, irregular or serrated outer surfaces so as to better engage the plastic bracket 14. The liner 14 of FIG. 7 is shown connected to a tooth 16, or the like.

Figure 8:
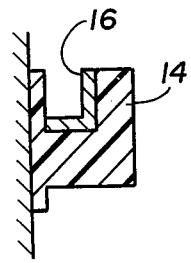

In FIG. 8 a modified liner 16 is shown which is generally L-shaped. In many instances, depending upon the types of forces applied to the bracket 14 by an arch wire, the liner 16 in the shape of a reverse L, is adequate for full protection to the bracket 14.

Figure 9:
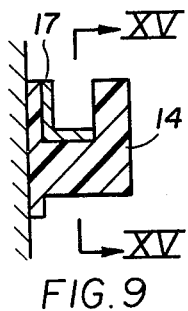

FIG. 9 shows a similar L-shaped liner 17 for use in a plastic bracket 14. Depending upon the application of forces, the liner 17 may adequately protect the plastic bracket 14.

The liners 15,16 and 17 are made of a harder material than the plastic 14, and are preferably of metal.

Figure 10:
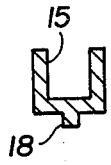
FIGS. 10-12 are cross-sectional views of modified liners for use in the embodiments shown in FIGS. 7-9.
Figure 11:
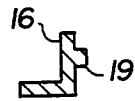
Figure 12:
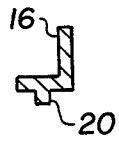

FIG. 10 shows a modified liner 15 having an extension member 18 extending therefrom for engagement within the plastic material 14. FIG. 11 shows a modified bracket 16 with a projecting member 19 and FIG. 12 shows a modified bracket 16 with a projecting member 20 at a different portion thereof. These liners of FIGS. 10–12 engage the respective brackets 14 in a manner similar to that shown in FIG. 4.

The various liners shown in the drawings are preferably of metal. However, they may be also suitably formed of extremely hard plastic material, such as glass-filled polycarbonate or any other suitable hard material which can protect the plastic bracket 1 from damage due to application of forces by arch wires, or the like.

The elongated composite structure of FIG. 6, which is to be later severed along lines 4,5 etc. to form individual brackets with liners therein, may be produced by molding an elongated length of plastic bracket material 1 and inserting an elongated length of liner 2 in an elongated opening in the elongated length of plastic material. The elongated liner 2 may be extruded, cast, molded, made from bent sheet material, stamped or be otherwise formed. Ultrasonic energy could be applied to the liner and/or bracket material as described above with respect to FIG. 1. Alternatively, an elongated length of liner material 2 may be formed by stamping, molding, casting, or other suitable method and may then be molded in the plastic to form an elongated composite structure. Another method of forming the device of the present invention is to fabricate an elongated length of liner 2 and to extrude a length of plastic bracket-shaped material over it. When the liner 2 is extruded, the plastic bracket may be either simultaneously or later extruded around it. The above described fabrication techniques are not limiting-other techniques could be used. In any event, the resultant structure would be generally as shown in FIG. 6. Similar fabrication techniques could be used for the liners of FIGS. 2–4 and for the bracket-liner configurations of FIGS. 7–12. Other combinations of the above fabrication steps could be used.

While the liner or inserts 2 have been shown as being tightly fit in the brackets by having a precise tight fit, by having interlocking shapes, by ultrasonic "welding" techniques, or by having a protrusion extending into the plastic material, it should be clear that the inserts or liners 2 may be adhered to the brackets by other techniques, such as by means of adhesives, or the like. While the walls of the liners have been shown as being substantially straight, they could be curved irregular or otherwise shaped.

If desired, a further insert or liner may be located under the tie wing portion of the bracket such as shown in FIG. 4. The additional inserts or liners 21,22 may be adhered to the bracket 1 by adhesive, ultrasonic welding, or the like, or may have a protruding portion, such as portion 10 of liner 9, which extends into the plastic material of the bracket to anchor the additional inserts 21,22 relative to the bracket. The inserts 21,22 are preferably coextensive with the width of the bracket so as to protect the bracket from chipping and breakage due to the presence of metallic tie wires, or the like, tied under the tie wings of the bracket. Since the inserts 21,22 are on the inner portions of the bracket, they are substantially not visible from the front, even when the bracket 1 is fabricated of translucent plastic material.

Figure 13:
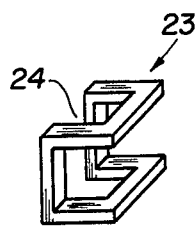
FIG. 13 illustrates a further modified bracket insert according to the present invention.

FIG. 13 illustrates a modified liner 23. The liner 23 is dimensioned so that it abuts against the edges of the bracket which define the arch wire receiving opening 3 (FIG. 1) to protect the edges of the bracket from damage. The central portions 24 of the bracket 23 are void spaces. Depending upon the forces involved, in some instances the liner 23 of FIG. 13 will provide adequate protection to the bracket in use. The bracket 23 of FIG. 13 may be made by casting, molding or stamping, depending upon the material from which it is made. The liner 23 may be made in an elongated structure, such as shown in FIG. 6, and severed at intervals along the length thereof either before or after insertion in a bracket member, such as an elongated bracket member.

Figure 14:
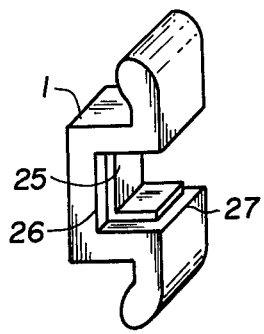
FIG. 14 illustrates a still further modified bracket insert according to the present invention.

FIG. 14 illustrates a still further modified liner 25 fabricated in accordance with the concepts of the present invention. The liner 25 is similar to the liner 2 of FIG. 1 but is dimensioned so that it extends a small distance short of the edges 26,27 of bracket 1. A key requirement of the bracket liner 25 of FIG. 14 is that it must be close enough to the edges so that an arch wire, when curving in normal usage, does not contact an unexposed edge of the bracket 1, or if it does contact an unexposed edge, it applies no substantial forces thereagainst which would otherwise damage the bracket edges. The central portions of the bracket liner 25 could be void spaces, such as spaces 24 of FIG. 13.

The liners of FIGS. 13 and 14 may be shaped in cross-section as the liners of FIGS. 2, 3, 4 or 10 to enhance engagement in the brackets.

The liners of FIGS. 7–12 may be modified to include void spaces in the central portions thereof, similar to liner 23 of FIG. 13, or to extend a small distance short of the edges of the bracket similar to the liner 25 of FIG. 14. It is necessary that the edges of the brackets subjected to forces of the arch wire to be protected from damage by the various liners.

Figure 15:
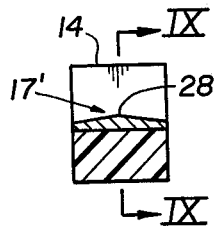
FIGS. 15 and 15a illustrates a modification of the bracket insert shown in FIG. 9.
Figure 15A:
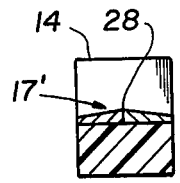

FIG. 15 shows a cross-section of the embodiment of FIG. 9 with the liner 17' having a triangulated cross-section forming a peak 28. This facilitates tipping of the arch wire and provides a still further improved bracket arrangement. The liner 17' can be fabricated in two pieces as shown in FIG. 15a.

The relative dimensions of the elements shown in the drawing have been exaggerated for ease of illustration and understanding of the inventive concept.

While the invention has been described above with respect to specific embodiments, it should be clear that the invention is not limited to the illustrated embodiments and may be freely modified within the spirit and scope of the invention as defined in the appended claims.

I claim:

1. An orthodontic bracket assembly comprising:
   a non-metallic bracket having an opening therein for receiving an arch wire, or the like; and
   a hard liner on at least a portion of the surface of said non-metallic bracket defining said opening for protecting said non-metallic bracket from damage due to forces applied by an arch wire, or the like, received therein, said liner being fabricated of a material harder than the material of said bracket;
   said liner having a raised peak portion interior of the edges of said opening which is adapted to serve as a tilting surface for an arch wire or the like, said liner being fabricated of two pieces which meet generally at said peak portion.

2. An orthodontic bracket according to claim 1 wherein said liner has a portion having a generally triangular cross-section the apex thereof being adapted to serve as said tilting surface.

3. An orthodontic bracket according to claim 1 wherein said liner extends a small distance short of the edges of the surface portion of said bracket which defines said opening.

4. An orthodontic bracket according to claim 1, wherein said bracket is fabricated from a hard plastic material, and said hard liner is a metal liner.

5. An orthodontic bracket assembly comprising:
   a non-metallic bracket having an opening therein for receiving an arch wire, or the like; and
   a hard liner on at least a portion of the surface of said non-metallic bracket defining said opening for protecting said non-metallic bracket from damage due to forces applied by an arch wire, or the like, received therein, said liner being fabricated of a material harder than the material of said bracket;
   said hard liner including flanges overlying a front surface portion of said bracket at least adjacent the area where said bracket opening opens to said front portion, said flanges extending from a liner portion in said opening.

6. An orthodontic bracket according to claim 5 wherein said first liner includes means for positively engaging said opening of said bracket.

7. An orthodontic bracket according to claim 5 wherein said liner substantially covers the complete surface portion of said bracket which defines said opening.

8. An orthodontic bracket according to claim 5, wherein said bracket is fabricated from a hard plastic material, and said hard liner is a metal liner.

9. An orthodontic bracket assembly comprising:
   a non-metallic bracket having an opening therein for receiving an arch wire, or the like; and
   a hard liner on at least a portion of the surface of said non-metallic bracket defining said opening for protecting said non-metallic bracket from damage due to forces applied by an arch wire, or the like, received therein, said liner defining a void space interior of the edges thereof, said liner being fabricated of a material harder than the material of said bracket.

10. An orthodontic bracket according to claim 9 wherein said liner extends a small distance short of the edges of the surface portion of said bracket which defines said opening.

11. An orthodontic bracket according to claim 9 wherein the outer edges of said space liner extend substantially to the edges of said opening of said bracket.

12. An orthodontic bracket according to claim 9, wherein said bracket is fabricated from a hard plastic material, and said hard liner is a metal liner.

13. An orthodontic bracket assembly comprising:
   a non-metallic bracket having an opening therein for receiving an arch wire, or the like, and tie wing portions;
   a first hard liner on at least a portion of the surface of said non-metallic bracket defining said opening for protecting said non-metallic bracket from damage due to forces applied by an arch wire, or the like, received therein, said liner being fabricated of a material harder than the material of said bracket; and
   at least one second hard liner on the rear surfaces of at least one of said tie wing portions, said at least one second hard liner being fabricated of a material harder than the material of said bracket.

14. An orthodontic bracket according to claim 13 wherein said hard lines are all fabricated from metal.

15. An orthodontic bracket according to claim 14 wherein said bracket is fabricated from hard plastic material.

16. An orthodontic bracket according to claim 13 wherein said bracket is fabricated from hard plastic material.

17. An orthodontic bracket according to claim 13 wherein said first liner includes flanges overlying a front surface portion of said bracket.

18. An orthodontic bracket according to claim 17 wherein said flanges overlie the front portion of said bracket adjacent the area where said bracket opening opens to said front portion.

19. An orthodontic bracket according to claim 13 wherein said first liner includes means for positively engaging said opening of said bracket.

20. An orthodontic bracket according to claim 19 wherein the outer surface of said first liner is irregularly shaped.

21. An orthodontic bracket according to claim 19 wherein said first liner has a protrusion thereon and said bracket receives said protrusion therein for anchoring of said first liner.

22. An orthodontic bracket according to claim 13 wherein said first liner is generally U-shaped.

23. An orthodontic bracket according to claim 13 wherein said first liner is generally L-shaped.

24. An orthodontic bracket according to claim 13 wherein said first liner substantially covers the complete surface portion of said bracket which defines said opening.

25. An orthodontic bracket according to claim 6 wherein the outer surface of said liner is irregularly shaped.

26. An orthodontic bracket according to claim 13 wherein said first liner extends a small distance short of the edges of the surface portion of said bracket which defines said opening.

27. An orthodontic bracket according to claim 20 wherein said liner includes means for positively engaging said opening of said bracket.

28. An orthodontic bracket according to claim 27 wherein the outer surface of said liner is irregularly shaped.

29. An orthodontic bracket according to claim 13 wherein said first liner defines a void space interior of the edges thereof.

30. An orthodontic bracket according to claim 29 wherein the outer edges of said first liner extend substantially to the edges of said opening of said bracket.

31. An orthodontic bracket according to claim 29 wherein said outer edges of said first liner extend to all of the edges of said opening of said bracket.

32. An orthodontic bracket according to claim 29 wherein said first liner includes means for positively engaging said opening of said bracket.

33. An orthodontic bracket according to claim 32 wherein the outer surface of said first liner is irregularly shaped.

34. An orthodontic bracket according to claim 13 wherein said hard liners are all of a material substantially harder than said bracket.

* * * * *